US008584715B2

(12) United States Patent (10) Patent No.: US 8,584,715 B2
Stoeckel et al. (45) Date of Patent: Nov. 19, 2013

(54) OPTICAL FILLING CONTROL OF PHARMACEUTICAL CAPSULES IN CAPSULE FILLING MACHINES

(75) Inventors: Peter Stoeckel, Appenheim (DE); Frank Biedenbender, Bingen (DE); Thomas Kruger, Ingelheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 853 days.

(21) Appl. No.: 12/668,350

(22) PCT Filed: Jul. 7, 2008

(86) PCT No.: PCT/EP2008/058734
§ 371 (c)(1),
(2), (4) Date: Jan. 26, 2010

(87) PCT Pub. No.: WO2009/007333
PCT Pub. Date: Jan. 15, 2009

(65) Prior Publication Data
US 2010/0192523 A1 Aug. 5, 2010

(30) Foreign Application Priority Data
Jul. 10, 2007 (EP) .................................... 07112146

(51) Int. Cl.
*B67C 3/02* (2006.01)
(52) U.S. Cl.
USPC ................. 141/95; 53/503; 73/1.74; 382/143; 250/577
(58) Field of Classification Search
USPC ....... 141/95; 73/1.73, 1.74; 53/503; 382/143; 250/577
See application file for complete search history.

(56) References Cited

U.S. PATENT DOCUMENTS 4,847,487 A 7/1989 Bordini
(Continued)

FOREIGN PATENT DOCUMENTS

| DE | 4441686 A1 | 6/1995 |
| DE | 102005049958 A1 | 4/2007 |
| GB | 1391221 A | 4/1975 |
| JP | 2001330412 A | 11/2001 |

(Continued)

OTHER PUBLICATIONS

International Search Report for PCT/EP2008/058734 mailed Oct. 7, 2008.

*Primary Examiner* — Jason K Niesz
(74) *Attorney, Agent, or Firm* — Michael P. Morris; Wendy A. Petka

(57) ABSTRACT

The present invention relates to a method for monitoring the filling of a capsule with a medicament, to a corresponding filling method, to the associated apparatuses, and to a computer program for controlling the method and the apparatus. In the monitoring method, after at least part of the capsule has been filled with a predefined filling mass of a predefined closed contour of the medicament, at least the filling mass in the part of the capsule after the filling operation is recorded using digital imaging in a first step, the contour of the filling mass in the part of the capsule is determined from the digital imaging recording in a second step, and the contour is analysed in a third step in order to assess the filling operation in comparison with the predefined contour. The invention provides for external influences on the image properties to be compensated for by controlling the optical system.

26 Claims, 7 Drawing Sheets

(56) References Cited

U.S. PATENT DOCUMENTS

| | | |
|---|---|---|
| 6,207,946 B1 | 3/2001 | Jusoh et al. |
| 2001/0054680 A1 | 12/2001 | Lindner |
| 2002/0051566 A1 | 5/2002 | Yamashita |
| 2005/0007588 A1* | 1/2005 | Tarozzi et al. ............... 356/337 |
| 2009/0146087 A1* | 6/2009 | Julius et al. ................ 250/577 |

FOREIGN PATENT DOCUMENTS

| | | |
|---|---|---|
| JP | 2002107309 A | 4/2002 |
| JP | 2003240545 A | 8/2003 |
| JP | 2004350963 A | 12/2004 |
| JP | 4350543 B2 | 10/2009 |
| RU | 2142860 C1 | 12/1999 |

* cited by examiner

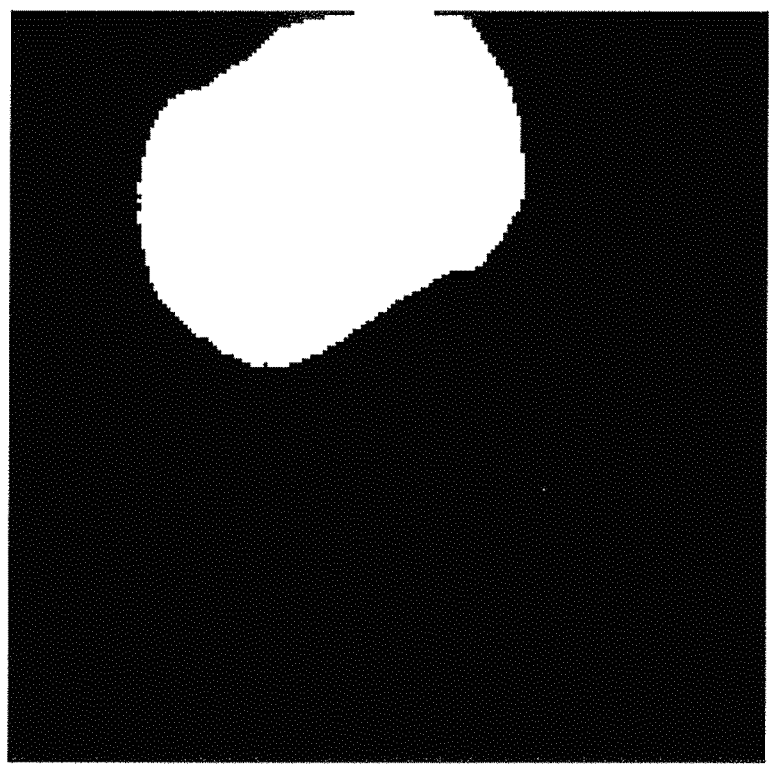
Fig. 6
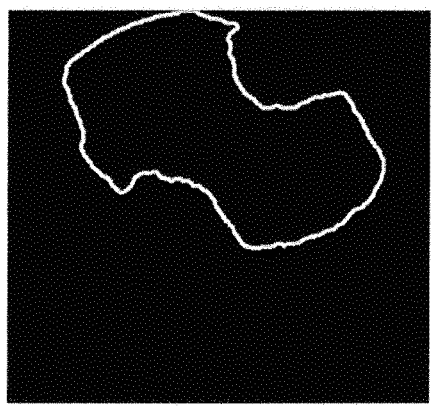 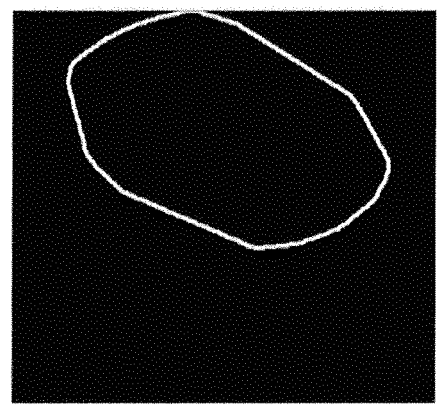
Fig. 7a                    Fig. 7b

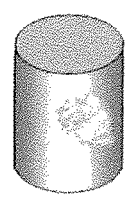
Fig. 9a          Fig. 10a
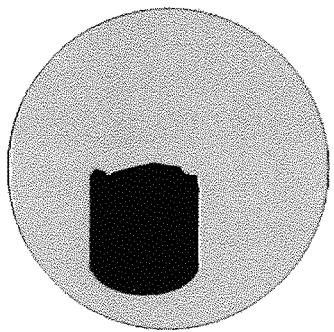
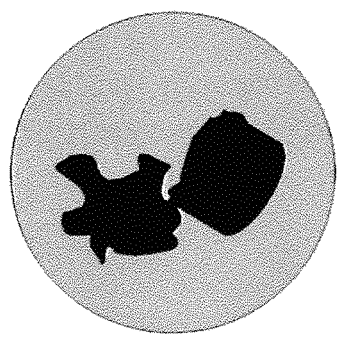
Fig. 9b          Fig. 10b

OPTICAL FILLING CONTROL OF PHARMACEUTICAL CAPSULES IN CAPSULE FILLING MACHINES

RELATED APPLICATIONS

This application is a 371 of International Application No. PCT/EP2008/058734, filed Jul. 7, 2008, which claims priority to European Patent Application No. 07112146.1, filed Jul. 10, 2007, the contents of which are incorporated herein by reference in their entirety.

The present invention relates to a process for monitoring the filling of a capsule with a medicament by image analysis, a corresponding filling process, the associated apparatus, and a computer programme for controlling the process.

Powdered oral and inhaled preparations are packed into capsules, e.g. hard gelatine capsules, in the pharmaceutical industry. The lower capsule parts that are to be filled are held in capsule carriers, particularly matrices, in the capsule filling machines. These capsule carriers are cylindrical template components made of stainless steel which are held and moved along by radial guide pins or a chain. The lower capsule part is located in a through-bore. A flange or a tapering in the diameter of the bore prevents the lower capsule part from slipping through. Various processes and machines are known for filling the capsules. These are all similar in that they operate volumetrically. A given metering volume is filled as homogeneously as possible with the medicament, which is generally in powder form. A loosely compacted cylinder of power is formed. This cylinder is then pressed out of the metering chamber and drops into the lower capsule part. The lower capsule part is sealed after filling by fitting on the cover.

The known capsule filling machines operate at a high throughput, filling up to 250000 capsules per hour with powder. The procedures used for quality control encompass random sampling of the capsules to check that they contain the correct amount of filling. The quality of the capsules is assessed on the basis of the random samples and corresponding statistical evaluation. Generally, the random sampling is done by weighing. A process of this kind is laborious, particularly for small fill quantities. In this case, in fact, the empty capsule also has to be weighed to obtain the tare weight. In addition, there is no 100% monitoring of the capsules.

There is therefore a fundamental need for a quality-control inspection of the capsules, which on the one hand allows 100% monitoring of all the capsules and on the other hand can be carried out, if possible, so that the process of filling or manufacturing the capsules is not slowed down by the inspection.

For example, a method and apparatus are known from U.S. Pat. No. 3,969,227 in which two light beams are shone through the capsules. The filling in the capsules interrupts the light beams. Therefore, using the intensity distribution in the beam transmitted, conclusions can be drawn as to the level of filling of the capsules with powder. This method has disadvantages in that it only provides a purely qualitative statement as to whether the capsule has been filled or not. Particularly with small fill quantities in the capsule the precision of the method is inadequate.

The publication "Automatische Füllkontrolle für die Abfüllung von Pellets in Hartgelatinekapseln" [Automatic filling monitoring for packing pellets into hard gelatine capsules] by W. Pfiefer, G. Marquardt and M. Rommel {Pharm. Ind. 49, No. 3, pages 291-297 {1987]) describes a method in which the surface of the filling of the lower part of a capsule is irradiated with a light beam and a spot of light is produced thereon. The level of filling of the capsule is determined by means of the size of the light spot that varies with the level of filling. This is the so-called Berghoff system. In another process discussed therein, the fill levels of a number of lower capsule parts are scanned using a scanning rod. If a rod is immersed too deeply this interrupts a light beam. This process is very inaccurate. Moreover, like the above mentioned process, it is suitable only for fillings that are homogeneously distributed in the lower part of the capsule. This latter process is suitable only for checking stationary capsules. The capsule has to be brought to a standstill after filling, which is technically laborious, and the manufacturing time is prolonged considerably.

From DE 10 2005 049 958 A1 a process for monitoring the filling of a capsule with a medicament is known, wherein the capsule or capsule parts are held and transported in capsules carriers, particularly matrices, and the contour of the fill mass is recorded by imaging using an optical system and the filling is evaluated by image analysis.

In order to be able to carry out virtually quantitative evaluation of the images, these must be as homogeneous as possible in their quality, i.e. the grey scale or chrominance distribution must remain as constant as possible. Changes in these image values during the operation of the capsule filling machine may result, for example, from the settling of dust, the changing of capsule carriers, capsule matrices or the replacement of optical components.

The objective of the present invention is therefore to provide a method of monitoring the filling of a capsule with a medicament and a method of this kind in conjunction with a filling operation, in which improved monitoring of the filling during the operation of the capsule filling machine is achieved by comparison with the prior art. An apparatus which is advantageous for achieving this aim is recited in the independent claim. The invention also sets out to provide a computer process for improving the performance and control of these methods and the apparatus. Some advantageous features are the subject of the independent claims.

This objective is achieved by detecting optical characteristics of the capsule carriers (matrices) and regulating the optical system using the evaluation of these characteristics. By adjusting the optical system in relation to the optical characteristics of each capsule carrier (capsule-carrying matrix) it is ensured that a quantitatively similar image quality, particularly grey scale or chrominance distribution, is obtained, so that a quantitative image evaluation at different capsule carrier locations or matrix locations leads to identical fill values.

One or more embodiments herein solves the problem of providing a process for the continuous machine filling of capsules with a medicament wherein at least part of the capsule is filled with a given fill mass of a given contour from the medicament and the optical characteristics of each capsule carrier are detected and stored in an electronic temporary memory and monitoring and regulation of the filling are carried out by the fact that the capsule or part of the capsule is optionally graded in accordance with the results of the monitoring.

One or more embodiments herein are directed to an apparatus for carrying out the processes.

One or more embodiments herein are directed to programme steps of a computer programme for carrying out the process and controlling the apparatus.

The process according to the invention serves to monitor the filling of a capsule with a medicament. It may be a hard gelatine capsule, for example. These capsules consist, for example, of a lower part and a cover.

In one embodiment, the capsule which is delivered for filling in a pre-closure position, for example, is separated into two parts by the application of a vacuum, before the monitoring process according to the invention. The lower capsule part, as an example of a part of a capsule which is to be filled, is filled with a given fill mass of a given closed contour.

The fill mass, in the case of a medicament already in powder form, is obtained from the metering volume and the density of the medicament. The medicament may be an orally administered or inhaled drug. The powder is lightly compacted in the metering chamber. The plug of powder generally survives the free fall from the metering device into the lower capsule part unharmed. The shape or sharp contour of the plug of powder is retained. In many cases, the metering volume and hence the fill mass formed therein are cylindrical.

To monitor the filling process, for example, an electronic camera and suitable optical means are directed into the open capsule part and an image is taken. For this purpose, the image is recorded directly by a camera equipped with a digital image converter or an electronic image of a camera is digitised using an additional converter. Depending on the camera used, a grey scale or chrominance image is taken. For example, the interior of the capsule is illuminated from above for the recording. Thus, a semi-reflecting mirror may be arranged above the capsule part to allow it to be simultaneously illuminated and recorded by means of this mirror.

During the image analysis the filling is evaluated. For this purpose, the contour is analysed in order to arrive at an evaluation of the filling in relation to the given closed contour of the shaped mass or metering volume. After the filling process, the filling, the medicament, is present as a compact cylindrical shape on the base of the capsules. Using the shape of the cylinder, evaluation can then take place according to the present invention. It has been observed that in cases where the metering chamber was not filled sufficiently, the metered fill material, the filling cylinder, broke into fragments. Thus, if the contour of the filling in the lower half of the capsule deviates substantially from the cylindrical form and/or if the contour is highly fractured, the filling has taken place with a change to the external contour of the fill mass, and defective filling has occurred. Thus the comparison of the contour with the intended contour allows judgments to be made as to the quality of the filling and permits a substantially quantitative evaluation of the filling. For example, unsatisfactory filling may occur if, during the release of the fill mass from the metering volume into the capsule part, there has been an incomplete release of the fill mass from the metering volume. Moreover, during the transfer of the fill mass into the capsule part, parts of the fill mass may have broken away, leading to incomplete filling. Moreover, there may have been some residual powder in the metering volume, which may lead to overfilling.

According to the present invention optical inspection of the filled capsules takes place in the machine shortly before the capsule is sealed. For this purpose the capsule is illuminated from above as already mentioned or illuminated from below through an access hole in the matrix.

It has been found that the capsule carriers, particularly matrices, differ in their optical properties depending on the design of the bore, the material and the surface characteristics. As a result, the brightness, grey scale and chrominance distribution may vary depending on the matrix location, the matrix number in the capsule filling machine. In long-term operation it is also possible for the machine components to become dusty when fine powders are being packaged. This dust settles on the inner surface of the through-bore in the matrices. It has been found that the light transmittance characteristics of the matrix are astonishingly dependent on the dust levels. A very dusty matrix scatters the light more, so that the integral light intensity in the camera image is reduced. However, to ensure reliable evaluation of the camera images, the integral light intensity in the images must be kept as constant as possible.

To ensure this, the optical characteristics of the capsule carriers are determined. By the optical characteristic of a capsule carrier is meant its reflectivity in incident light, or its transmittance qualities when light is shone through an aperture. The reflectivity and transmittance qualities are determined either by running the capsule filling machine empty with no capsules inserted, or running it empty with empty capsule components. It is particularly advantageous to determine the reflectivity and transmittance during operation of the capsule filling machine. The characteristics of reflectivity and transmittance are measure with the lower capsule part and filling inserted. The characteristics may be determined using a photosensitive element such as a photo-resistor, a phototransistor or a photodiode, for example, that measures the intensity of the scattered light, or in the case of transmittance, of the light passing through.

Advantageously it is also possible to calculate the reflected or transmitted light intensity from the image data recorded by totalling or averaging out the image matrix or parts of the image matrix, so as to determine the actual optical characteristic of a capsule carrier, or a matrix location in the machine. This is achieved by assigning a specific reflectivity value or specific transmittance value or a specific proportional light intensity value to each matrix, or each location for receiving a capsule. These values are stored in a memory, particularly a temporary memory.

On the basis of the characteristics stored in the memory it is envisaged that the optical components can be regulated.

According to the invention, for this purpose, the intensity of the light source used for each image taking is regulated so that the light intensity conforms to a desired value.

The desired value is determined for example by averaging over one filling run, the random sampling number of which corresponds to the number of matrix filling locations in the machine, or over a number of runs. If a light emitting diode, particularly a high performance LED, is used as the light source, a voltage characteristic that is proportional to the required intensity is taken from the voltage intensity characteristic of the diode in order to adapt the light intensity, and the diode is controlled with this voltage value. The diode characteristic is stored in the control for this purpose. Regulation is carried out by means of a voltage or current source that can be controlled by computer.

Advantageously, the light emitting diode is operated in pulsed manner, i.e. a voltage is only applied to the diode for the duration of the illumination. This enables significantly higher maximum voltages to be applied to the diode for short periods, without damaging the diode, particularly as a result of overheating. Advantageously, the diode can thus be operated over a wide range of intensities, so that even major variations in the transmittance properties of the capsule carriers or matrices can be evened out.

In addition to or alternatively to the control of the light source described above it is also possible to control the shutter speed of the image camera accordingly so as to achieve a desired level of light intensity in the image. Preferably, CCD cameras or CMOS image converters with refresh rates of 10-1000 Hertz and an electrical shutter speed of 1 microsecond to 100 milliseconds are used. Advantageously, illumination times, i.e. actuation times of the light emitting diode and/or camera shutter speeds of 10 microseconds-100 microseconds, most preferably 30-70 microseconds, are chosen.

Adjusting the optical system in relation to the optical characteristics of each capsule carrier ensures that for each capsule carrier, each matrix location in the capsule filling machine qualitatively equal image quality, particularly grey scale or chrominance distribution is obtained, so that a quantitative image evaluation at different capsule carrier locations or matrix locations results in identical fill values.

Advantageously, the process is controlled using a computer programme installed in a process computer in the apparatus. Using this software, the integral light intensity in the images is continuously monitored and recorded for each matrix number. The mean integral light intensity of the images from each individual matrix is the input variable for a regulating algorithm which determines the deviation of the light intensity from the desired value and adjusts the LED voltage so that the actual intensity in the image gradually comes closure to the desired value. Thus, for each matrix, there is a regulating algorithm and a time-variable matrix-specific LED voltage.

For examining the contour it may be advantageous to computer-correct or standardise the images obtained, which are in the process computer as an image matrix. For example, each pixel in a grey scale image is laid down by a numerical value between 0 and 255. If only grey scale values of between 50 and 200 are obtained when measuring an individual image, these values can be standardised by computer to 0 to 255, i.e. spread out so as to illuminate the image more intensively. The image data and also other process data such as the level of fullness of the capsule, the light intensity and control voltages are visualised online on a monitor to provide the operating staff with additional information as to the status of the capsule filling apparatus.

The measured values of the optical fill monitoring can be compared with the data of the tare weigh measurements in order to carry out calibration of the data of the optical fill monitoring using the tare measurements.

The invention further relates to a process for the continuous mechanical filling of capsules with a medicament, in which in each case at least part of the capsule is filled with a given fill mass of a given contour from the supply of medicament and moreover the filling is monitored according to one of the embodiments described above. During continuous mechanical filling this is carried out by the so-called inline method, i.e. the filling is carried out in the manner of a conveyor belt. The monitoring process in the embodiments described above allows total monitoring of the capsules, in synchronism with the filling process, thanks to the comparatively high speed at which the detection and analysis of the fill mass take place. For example, filling processes of this kind operate with a delivery rate of 80,000 capsules per hour. As the monitoring process according to the invention takes a period of considerably less than 45 ms to monitor a single capsule, the monitoring process according to the invention can easily be combined with the known filling processes to achieve a total and effective quality control. The filling process may be, for example, a so-called packing process in which the metering volume is provided with matrix discs having corresponding bores. Depending on the results of the monitoring the respective capsule is rejected if necessary. For example, the capsule or the filled lower capsule part is ejected from the stream of other capsules by a jet of air during further transportation.

In one embodiment the capsule deemed to be defectively filled is rejected after a delay of about 450 ms after filling. In the mean time, for example, the sealing of the lower capsule part is completed or it is transported on for packaging. This allows sufficient time for any possible delay in evaluation.

Filling is carried out using the pipette principle. The pipette principle is described below by reference to an example. Whereas in the packing process the metering volume is formed by matrix discs with corresponding bores, in the pipette the metering volume is produced by a defined withdrawal of a steel plunger in a steel sleeve. Then the pipette is immersed to a specified depth in a bed of powder consisting of the medicament, this powder being as homogeneous as possible. Powder is forced into the cylindrical metering volume which is open at the bottom until the powder totally fills the volume and thus forms a cylindrical fill mass. The pipette is then removed from the bed of powder. It passes through a suction pathway in which it is freed from any powder adhering externally. At the same time the open bottom of the pipette slides over a carefully aligned flat surface. In this way the excess powder is also removed from the bottom and the bottom of the powder cylinder in the metering volume is smoothed off. The pipette emerges from the suction pathway and a little later assumes a position directly above an open lower capsule part. The plunger of the pipette then forces the powder cylinder, which has a precisely defined volume, out of the metering chamber. An abrupt upward and downward movement of the plunger causes the powder cylinder to detach itself from the endface of the plunger. The distance of, for example, about 14 mm to the bottom of the lower capsule part is traveled by the cylindrical fill mass in free fall. It has been shown that the monitoring process according to the invention can advantageously be combined with the pipette process.

FIG. 6 is an illustration of the fill mass of FIG. 5, whereby the greyscale image has pixelated into a binary image;

FIG. 7a is an illustration of an original contour of another fill mass based on binary data obtained in a similar way as in FIG. 6;

FIG. 7b is an illustration of an approximated contour of the contour of FIG. 7a, based on a convex envelope;

FIG. 9a is an illustration of a fill mass of powder that has not properly fallen off a plunger;

FIG. 9b is an illustration of a recorded image of the fill mass of powder of FIG. 9a;

FIG. 10a is an illustration of a fill mass of powder that is not of homogeneous density throughout;

FIG. 10b is an illustration of a recorded image of the fill mass of powder of FIG. 10a in a downstream process;

FIG. 11b is an illustration of a recorded image of the fill mass of powder of FIG. 11a;

FIG. 12b is an illustration of a recorded image of the fill mass of powder of FIG. 12a.

Figure 1:
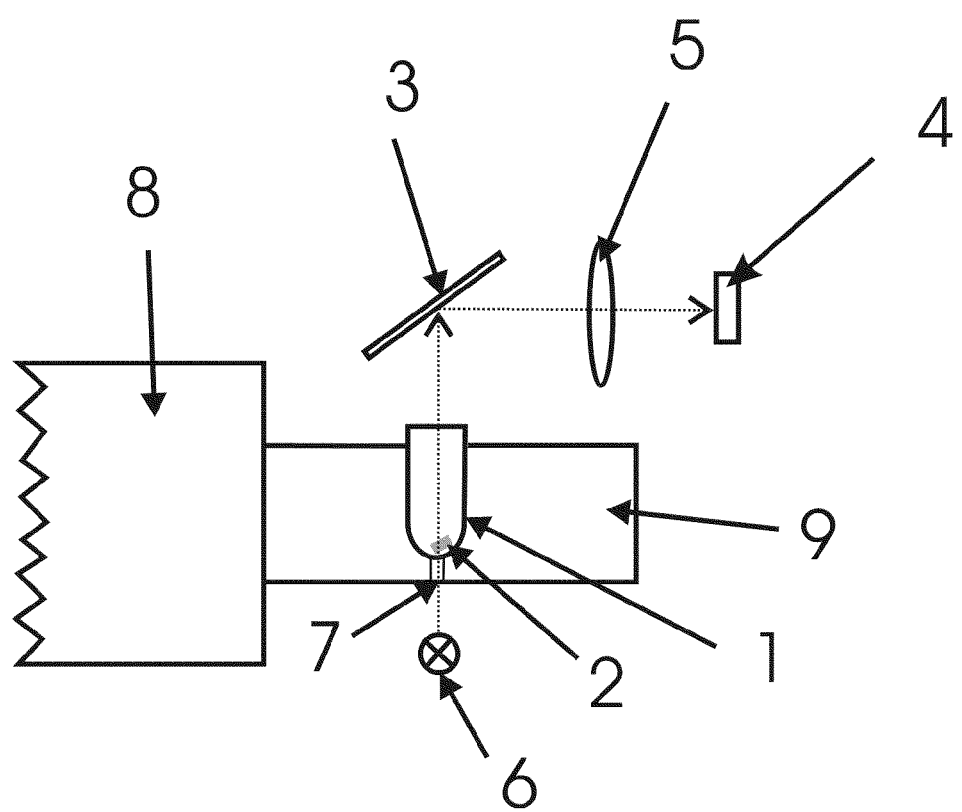
FIG. 1 is a schematic diagram illustrating an apparatus for carrying out a process for monitoring and filling capsules.

An embodiment of the monitoring process according to the invention which is used together with a filling process operating by the pipette principle is described below. A detail of the associated apparatus is schematically shown in FIG. 1.

The lower capsule parts 1 are each placed in stainless steel matrices which are in turn held by the carriage 9 of a transporting system 8 of the filling installation. These carriages 9 travel along circular tracks, with cam control, in a horizontal plane underneath the pipettes (not shown). On this track, just behind the position where the lower capsule part 1 is filled with the fill mass consisting of powder, there is a region in which the carriages 9 with the matrix are largely exposed and easily accessible. Using a CCD camera 4 and associated optical means 3, 5, an image of the open lower capsule part 1 is recorded from above shortly after filling has taken place and the images are passed on for evaluation. For this purpose the camera images are transmitted to a computer and evaluated therein using a suitable algorithm. To assist with the evaluation of the images and, in particular, to make them as error-proof as possible, the images have increased contrast. In this respect it is not a good idea to illuminate the fill mass 2 in the lower capsule part 1 solely from above. Instead, it has proved advantageous to illuminate the lower capsule part 1 from below with an intense flash of light and to record the image with back light, as shown by the dotted arrows in FIG. 1. For this, there is a through-hole 7 in the carriage 9 and in the matrices in which the lower capsule parts 1 are held. The lower capsule part 1 is illuminated by means of a light-emitting diode 6 arranged underneath the plane of movement of the carriage 9.

Above the plane of movement of the carriage there is a mirror 3 which reflects the light transmitted through the lower capsule part 1 at right-angles and is projected through an objective 5 onto the CCD chip 4 of a camera. The carriages with the lower capsule parts travel at a track speed of about 1.30 m/s between the light source and mirror. As the capsules have a diameter of only about 5 mm, a correspondingly large imaging scale is used. To ensure that sufficiently sharp images are obtained even under these conditions, correspondingly short camera exposure times are used. To achieve a good signal to noise ratio in spite of the short integration time of the CCD chip 4 and to avoid having to open the shutter of the objective too widely in the interests of adequate sharpness, the capsule is illuminated with very intense light from an LED 6. It has been found that corresponding light intensities can be obtained easily and reliably using light emitting diodes (LEDs). The camera exposure time is 50 µs, for example. During this time the lower capsule part is moved on by about 65 µm. The blurring of the image caused by the motion is negligible.

Figure 2:
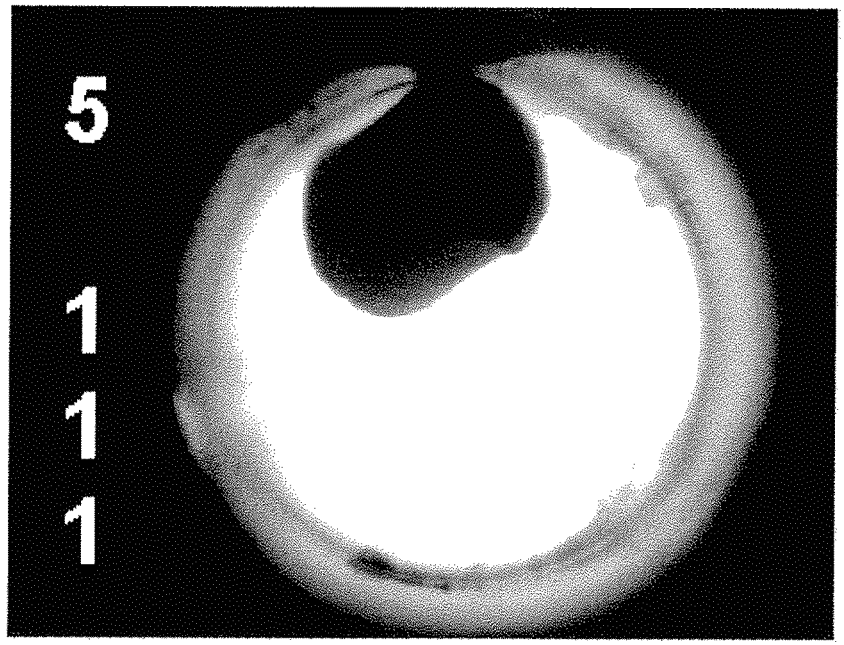
FIG. 2 is an illustration of a fill mass of a capsule that has been subject to the apparatus of FIG. 1.
Figure 3:
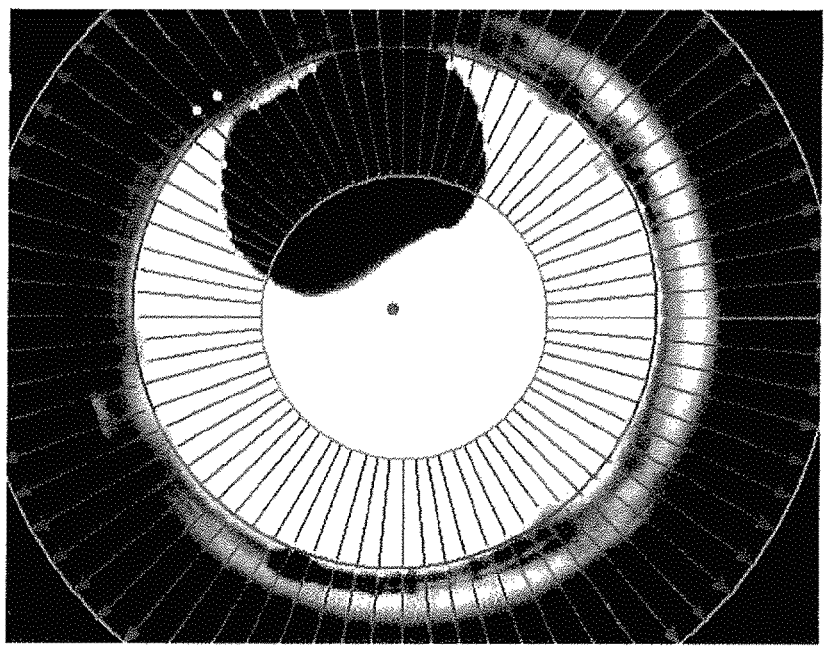
FIG. 3 is another illustration of the fill mass of the capsule of FIG. 2 from another perspective.
Figure 4:
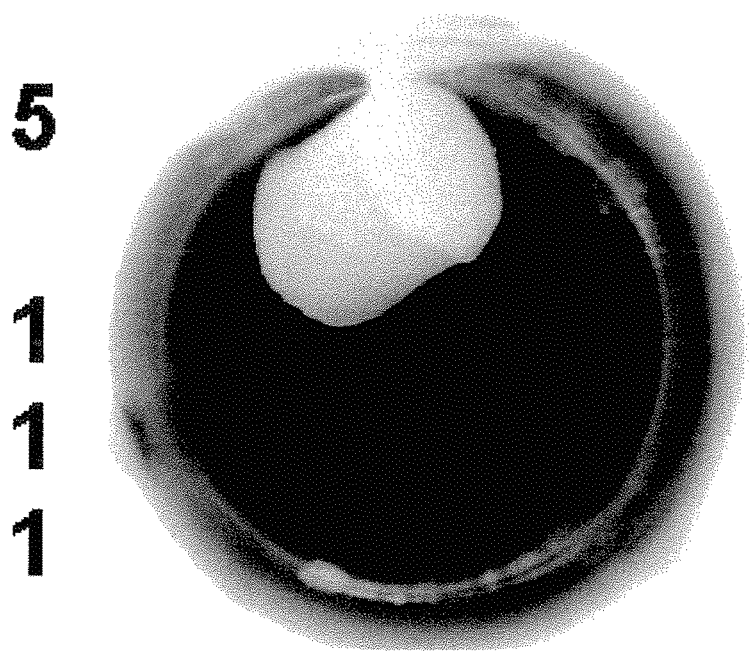
FIG. 4 is an illustration of the fill mass of the capsule of FIG. 2, whereby the image greyscale has been inverted.
Figure 5:
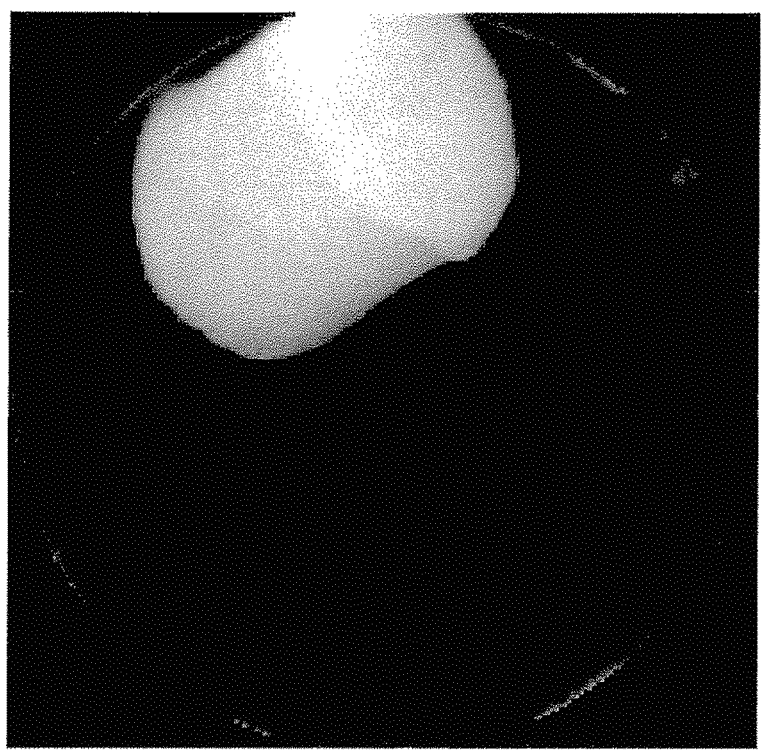
FIG. 5 is an illustration of the fill mass of FIG. 4, whereby the image has been masked to primarily illustrate the fill mass without eh capsule details.
Figure 8A:
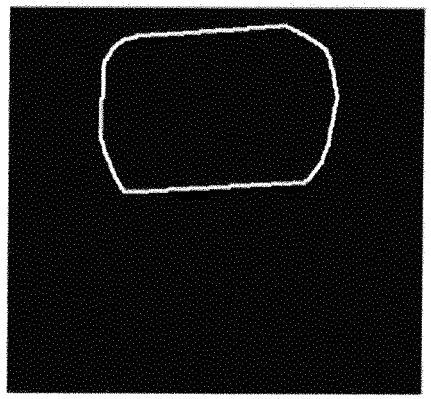
FIG. 8a is an illustration of an original contour of yet another fill mass based on binary data obtained in a similar way as in FIG. 6.
Figure 8B:
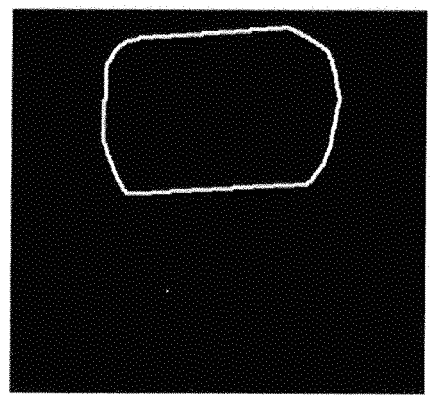
FIG. 8b is an illustration of an approximated contour of the contour of FIG. 8a, based on a convex envelope.

Specifically, the Image Processing Comprises the Following Steps:

1. A camera records a grey scale image, and an identifier is faded into the image in order to provide a clear allocation of capsule part to image, as shown in FIG. 2.
2. As the lower capsule parts may not always be seen in the same position, the capsule is located in the image, as shown in FIG. 3.
3. The image is inverted, as shown in FIG. 4.
4. Then the image is masked so that only the region inside the capsule still remains, as shown in FIG. 5.
5. The grey scale image is converted into a binary image using a suitably fixed threshold value, as shown in FIG. 6.
6. A broken fill mass is characterised in that the contour of the circumference has concave regions. The concave regions are detected by means of the convexity parameter. FIGS. 7a and 8a each show the original contour, i.e. The recorded contour. FIGS. 7b and 8b each show a shape of the recorded contour, approximated by a convex envelope. The convexity parameter alpha is equal to the quotient of the circumference of the convex approximation and the circumference of the original contour. In the case of FIGS. 7a and 7b, for example, an alpha value of 0.903 is obtained, whereas the alpha value of FIGS. 8a and 8b is 0.994. Accordingly, FIG. 7a or 7b corresponds to a defective filling of the lower capsule part, whereas FIGS. 8a and 8b correspond to satisfactory filling with an alpha value of roughly 1.

FIGS. 9a, 9b, 10a and 10b illustrate the correlations between damaged fill mass, underfilled capsule and recorded contour. In FIG. 9a the fill mass consisting of powder has not properly fallen off the plunger. Some of the fill mass is still suspended. This may be due to the unfavourable adhesion characteristics of the powder, for example. During the recording, i.e. after filling and as shown in FIG. 9b, the fill mass per se has not broken up further but has fractured as a result of the partial breakaway from the plunger and is found to be defective by the monitoring process. In FIG. 10a the density of the fill mass is inhomogeneous, i.e. too low in parts, so that the density averaged over the entire volume is too low. This may be due, for example, to an inhomogeneous bed of powder or poorly filled insertion holes. As shown in FIG. 10b, the plug of powder has broken into several fragments after filling and during recording, as a result of insufficient stability, and defective filling can be detected particularly easily, among other things, by the presence of the fragments.

Figure 11A:
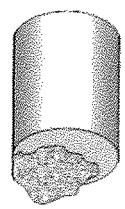
FIG. 11a is an illustration of a shape of a fill mass of powder that is difficult to monitor.
Figure 11B:
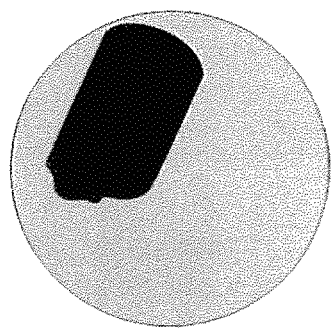

FIGS. 11a, 11b, 12a and 12b illustrate the correlations between a damaged fill mass, an overfilled capsule and a recorded contour. In FIG. 11a the underside of the fill mass is not cleanly imaged. This may be due to a poorly arranged suction pathway, for example. During recording, i.e. after filling and as shown in FIG. 11b, the fill mass itself has not broken up, but because of the untidy shape at the bottom the shadow in the image is too large and too fractured. Therefore the monitoring process grades the capsule associated with the image as being a defective capsule.

Figure 12A:
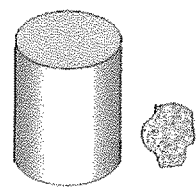
FIG. 12a is an illustration of a shape of a fill mass of powder that includes unwanted particles.
Figure 12B:
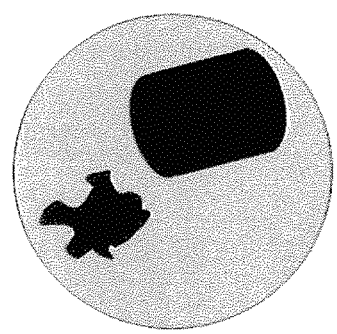

FIG. 12a shows that besides the actual fill mass, additional secondary particles get into the lower capsule part. This may be due to powder adhering to parts of the metering device, soiled matrix discs and accumulations of powder above the tip of the plunger. During recording, i.e. after filling and as shown in FIG. 12b, the fill mass itself has not broken up. The secondary lumps are recognised by the image evaluation algorithm. If the area of these lumps is above a defined limit, the capsule probably contains too much powder and is deemed "defective".

7. Dust in the capsule filling machine has the effect that the optical properties of the system, particularly the light intensity of the images, may change. Thus, different capsule carriers or different matrices may have different transmittance characteristics as a result of their surface nature. These differences are further aggravated by dust in the equipment. As the apparatus operates continuously, there is no opportunity for cleaning between maintenance visits.

Figure 13:
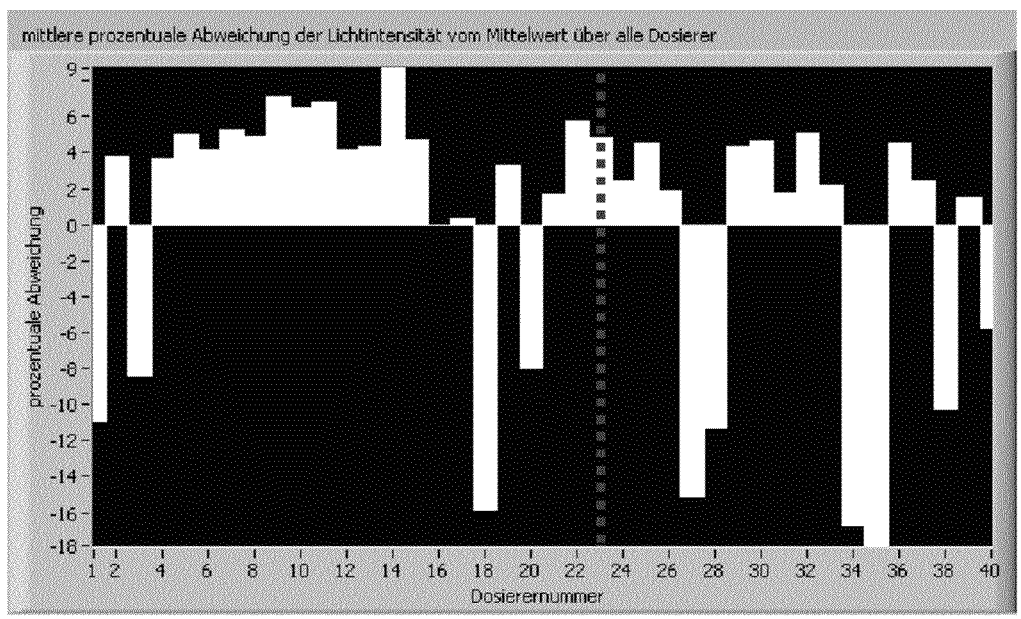
FIG. 13 is an illustration of integral light intensity of image taken within the apparatus of FIG. 1.

In practice, it has been found that the matrices accumulate dust to very different extents. The reason for this is in the individually different surface qualities of the matrix bores and in the mechanical variability in the region of the vacuum dust removal system inside the machine. Consequently, the differences in the transmittance properties of the individual matrices during continuous operation of the machine continue to increase steadily until gradually there is a "stationary" layer of dust. This process can also lead to a difference of 30 percent or more in the integral light intensity in the images originating from certain matrices, as shown in FIG. 13. Using a computer programme, the integral light intensity in the images is constantly monitored and recorded for each matrix number, as can be seen from FIG. 13. The mean integral light intensity of the images from each individual matrix is the input variable for a regulating algorithm that determines the deviation of the light intensity from the desired value and adjusts the LED voltage such that the actual intensity in the image gradually converges with the desired value. Thus, for each matrix there is precisely one regulating algorithm and a time-variable, matrix-specific LED voltage. After the evaluation of each image, the software for the current matrix sends the desired value for the LED voltage to an SPC via a bus that is specially designed for this purpose. Here, the value is filed in an addressable register.

In the mean time the metering head in the machine continues to revolve. As soon as the matrix in question has returned the camera position, the SPC calls up the desired value for the LED voltage for this matrix from the register and adjusts the voltage accordingly.

On each revolution of the metering head of the machine, the matrix-specific LED voltages are newly adapted. In this way, the differences in the integral light intensity of FIG. 13 are constantly levelled until they have virtually disappeared. If during continuous operation of the machine the transmittance properties of the matrices gradually alter as a result of a build-up of dust, the regulating algorithm takes account of this process by constantly correcting the LED voltage.

The process according to the invention is used particularly preferably for capsules that contain powdered medicaments for inhalation, so-called inhalants. These powdered medicaments may contain an active substance in admixture with a physiologically acceptable excipient.

Examples of physiologically acceptable excipients include, for example, monosaccharides (e.g. glucose or arabinose), disaccharides (e.g. lactose, saccharose, maltose or trehalose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose, glucose or trehalose is preferred, preferably lactose or glucose, particularly, but not exclusively, in the form of their hydrates. For the purposes of the invention, lactose is the particularly preferred excipient, while lactose monohydrate is most particularly preferred.

The excipients mentioned are usually characterised in that the excipient has an average particle size of 10-50 μm.

By average particle size is meant here the 50% value of the volume distribution measured with a laser diffractometer using the dry dispersion method.

The percentages given within the scope of the present invention are always percent by weight, unless specifically stated to the contrary.

In partic preferred inhalant powders the excipient is characterised by an average particle size of 12 to 35 μm, particularly preferably 13 to 30 μm.

Alternative pharmaceutical compositions are further characterised in that the excipient consists of a mixture of coarser excipient with an average particle size of 17 to 50 μm, particularly preferably from 20 to 30 μm and finer excipient with an average particle size of 2 to 8 μm, particularly preferably from 3 to 7 μm. Inhalant powders in which the proportion of finer excipient in the total quantity of excipient is from 3 to 15%, most preferably 5 to 10%, are particularly preferred.

When reference is made to a mixture within the scope of the present invention, this always means a mixture obtained by mixing together clearly defined components. Accordingly, when an excipient mixture of coarser and finer excipient fractions is mentioned, this can only denote mixtures obtained by mixing a coarser excipient component with a finer excipient component.

The coarser and finer excipient fractions may consist of chemically identical or chemically different substances, while inhalable powders in which the coarser excipient fraction and the finer excipient fraction consist of the same chemical compound are preferred.

For the application of the inhalant powders according to the invention using powder-filled capsules it is preferable to use capsules the shell of which is made from gelatine, cellulose derivatives, starch, starch derivatives, chitosan or synthetic plastics.

If gelatine is used as the capsule material, it may be used in admixture with other additives selected from among polyethyleneglycol (PEG), preferably PEG 3350, glycerol, sorbitol, propyleneglycol, PEO-PPO block copolymers and other polyalcohols and polyethers. Within the scope of the present invention it is particularly preferable to use gelatine in admixture with PEG, preferably PEG 3350. A gelatine capsule according to the invention preferably contains PEG in an amount of 1-10% (wt.-%), preferably 3-8%. Particularly preferred gelatine capsules contain PEG in an amount of 4-6%, a PEG content of about 5% being most preferred according to the invention.

If cellulose derivatives are used as the capsule material, it is preferable to use hydroxypropylmethylcellulose, hydroxypropylcellulose, methylcellulose, hydroxymethylcellulose and hydroxyethylcellulose. In this case, hydroxypropylmethylcellulose (HPMC), particularly preferably HPMC 2910 is used as the capsule material.

If synthetic plastics are used as the capsule material, these are preferably selected according to the invention from among polyethylene, polycarbonate, polyester, polypropylene and polyethylene terephthalate. Particularly preferred synthetic plastics for the capsules for inhalation according to the invention are polyethylene, polycarbonate or polyethylene terephthalate. If polyethylene is used as one of the particularly preferred capsule materials according to the invention, polyethylene with a density of between 900 and 1000 $kg/m^3$, preferably from 940-980 $kg/m^3$, particularly preferably 960-970 $kg/m^3$ is preferably used (high-density polyethylene).

The synthetic plastics according to the invention may be processed in various ways using production methods known in the art. The processing of plastics by injection moulding is preferred for the purposes of the invention. Injection moulding without the use of mould release agents is particularly preferred. This production method is well-defined and is characterised by being particularly reproducible.

These capsules may preferably contain about 1 to 20 mg, preferably about 3 to 15 mg, particularly preferably about 4 to 12 mg of inhalant powder. Preferred formulations according to the invention contain 4 to 6 mg of inhalant powder. Of equivalent importance are capsules for inhalation that contain the formulations according to the invention in an amount of from 8 to 12 mg.

The active substances that may be contained in the powdered medicaments are preferably selected from among the betamimetics, anticholinergics, corticosteroids, PDE4 inhibitors, LTD4 antagonists, EGFR-inhibitors, dopamine agonists, H1-antihistamines, PAF antagonists and PI3-kinase inhibitors.

The betamimetics used here are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzyl-sulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]-sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one, 1-(4-ethoxy-carbonylamino-3-cyano-5-fluorophenyl)-2-(tert.-butylamino)ethanol, 2-hydroxy-5-(1-hydroxy-2-{2-[4-(2-hydroxy-2-phenyl-ethylamino)-phenyl]-ethylamino}-ethyl)-benzaldehyde, N-[2-hydroxy-5-(1-hydroxy-2-{2-[4-(2-hydroxy-2-phenyl-ethylamino)-phenyl]-ethylamino}-ethyl)-phenyl]-formamide, 8-hydroxy-5-(1-hydroxy-2-{2-[4-(6-methoxy-biphenyl-3-ylamino)-phenyl]-ethylamino}-ethyl)-1H-quinolin-2-one, 8-hydroxy-5-[1-hydroxy-2-(6-phenethylamino-hexylamino)-ethyl]-1H-quinolin-2-one, 5-[2-(2-{4-[4-(2-amino-2-methyl-propoxy)-phenylamino]-phenyl}-ethylamino)-1-hydroxy-ethyl]-8-hydroxy-1H-quinolin-2-one, [3-(4-{6-[2-hydroxy-2-(4-hydroxy-3-hydroxymethyl-phenyl)-ethylamino]-hexyloxy}-butyl)-5-methyl-phenyl]-harnstoff, 4-(2-{6-[2-(2,6-dichloro-benzyloxy)-ethoxy]-hexylamino}-1-hydroxy-ethyl)-2-hydroxymethyl-phenol, 3-(4-{6-[2-hydroxy-2-(4-hydroxy-3-hydroxymethyl-phenyl)-ethylamino]-hexyloxy}-butyl)-benzylsulphonamide, 3-(3-{7-[2-hydroxy-2-(4-hydroxy-3-hydroxymethyl-phenyl)-ethylamino]-heptyloxy}-propyl)-benzylsulphonamide, 4-(2-{6-[4-(3-cyclopentanesulphonyl-phenyl)-butoxy]-hexylamino}-1-hydroxy-ethyl)-2-hydroxymethyl-phenol, N-adamantan-2-yl-2-(3-{2-[2-hydroxy-2-(4-hydroxy-3-hydroxymethyl-phenyl)-ethylamino]-propyl}-phenyl)-acetamide, optionally in the form of their racemates, enantiomers, diastereomers and optionally in the form of their pharmacologically acceptable acid addition salts, solvates or hydrates. The preferred acid addition salts of the betamimetics according to the invention are those selected from among the hydrochloride, hydrobromide, hydriodide, hydrosulphate, hydrophosphate, hydromethanesulphonate, hydronitrate, hydromaleate, hydroacetate, hydro-citrate, hydrofumarate, hydrotartrate, hydrooxalate, hydrosuccinate, hydrobenzoate and hydro-p-toluenesulphonate.

The anticholinergics used here are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine and aclidinium, preferably as the bromide salt.

Other anticholinergics which are preferably used are selected from among tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide, tropenol 9-hydroxy-fluorene-9-carboxylate methobromide, tropenol 9-fluoro-fluorene-9-carboxylate methobromide, scopine 9-hydroxy-fluorene-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, cyclopropyltropine methyl 4,4'-difluorobenzilate methobromide, tropenol 9-hydroxy-xanthene-9-carboxylate methobromide, scopine 9-hydroxy-xanthene-9-carboxylate methobromide, tropenol 9-methyl-xanthene-9-carboxylate-methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide and scopine 9-hydroxymethyl-xanthene-9-carboxylate methobromide. The above-mentioned methobromides may also be used as salts within the scope of the present invention, by using, instead of the methobromide, the metho-X salts, wherein X is selected from among the fluoride, chloride, iodide, sulphate, phosphate, methanesulphonate, nitrate, maleate, acetate, citrate, fumarate, tartrate, oxalate, succinate, benzoate and p-toluenesulphonate.

The corticosteroids used here are preferably compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26, (S)-fluoromethyl 6,9-difluoro-17-[(2-furanylcarbonyl)oxy]-1'-hydroxy-16-methyl-3-oxo-androsta-1,4-diene-17-carbothionate, (S)-(2-oxo-tetrahydro-furan-3S-yl) 6,9-difluoro-1'-hydroxy-16-methyl-3-oxo-17-propionyloxy-androsta-1,4-diene-17-carbothionate and cyanomethyl 6α,9α-difluoro-11β-hydroxy-16α-methyl-3-oxo-17α-(2,2,3,3-tetramethylcyclopropylcarbonyl)oxy-androsta-1,4-diene-17β-carboxylate, optionally in the form of the racemates, enantiomers or diastereomers thereof and optionally in the form of the salts and derivatives thereof, the solvates and/oder hydrates thereof. Any reference to steroids includes a reference to any salts or derivatives, hydrates or solvates thereof that may exist. Examples of possible salts and derivatives of steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

The PDE4 inhibitors used here are preferably compounds selected from among enprofyllin, theophyllin, roflumilast, ariflo (cilomilast), oglemilast, tofimilast, pumafentrin, lirimilast, arofyllin, atizoram, D-4418, Bay-198004, BY343, CP-325,366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370, N-(3,5-dichloro-1-oxo-pyridin-4-yl)-4-difluoromethoxy-3-cyclopropylmethoxybenzamide, (−)$_p$-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-5-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]acetate, (S)-(−)-ethyl[4-(3-cyclopentyloxy-4-methoxyphenyl)pyrrolidin-2-ylidene]acetate, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of their racemates, enantiomers, diastereomers and optionally in the form of their pharmacologically acceptable acid addition salts, solvates or hydrates. The preferred acid addition salts according to the invention are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4 antagonists used here are preferably compounds selected from among montelukast, pranlukast, zafirlukast, MCC-847 (ZD-3523), MN-001, MEN-91507 (LM-1507), VUF-5078, VUF-K-8707, L-733321, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorthieno[3,2-b]pyridin-5-yl)-(E)-ethenyl)phenyl)-3-(2-(1-hydroxy-1-methylethyl)phenyl)propyl)thio)methyl)cyclopropane-acetic acid and [2-[[2-(4-tert-butyl-2-thiazolyl)-5-benzofuranyl]oxymethyl]phenyl]acetic acid, optionally in the form of their racemates, enantiomers, diastereomers and optionally in the form of their pharmacologically acceptable acid addition salts, solvates or hydrates. The preferred acid addition salts according to the invention are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

By salts or derivatives which the LTD4 antagonists may possibly be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

The EGFR-inhibitors used here are preferably compounds selected from among cetuximab, trastuzumab, ABX-EGF, Mab ICR-62, 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluorophenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluorophenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluorophenyl)amino]-6-{[4-(R)-2-methoxymethyl-6-oxo-morpholin-4-yl)-1-oxo-2-buten-1-yl]amino}-7-cyclopropylmethoxy-quinazoline, 4-[(3-chloro-4-fluorophenyl)amino]-6-[2-(S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-to-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)

methoxy]-quinazoline, 4-[(3-ethinyl-phenyl)amino]-6,7-to-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluorobenzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-(R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline, 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluorophenyl)amino]-6-[2-(2,2-dimethyl-6-oxo-morpholin-4-yl)-ethoxy]-7-methoxy-quinazoline, 4-[(3-chloro-4-fluorophenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluorophenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluorophenyl)amino]-6-{2-[4-(2-oxo-morpholin-4-yl)-piperidin-1-yl]-ethoxy}-7-methoxy-quinazoline, 4-[(3-chloro-4-fluorophenyl)amino]-6-[1-(tert.-butyloxycarbonyl)-piperidin-4-yloxy]-7-methoxy-quinazoline, 4-[(3-chloro-4-fluorophenyl)amino]-6-(trans-4-amino-cyclohexan-1-yloxy)-7-methoxy-quinazoline, 4-[(3-chloro-4-fluorophenyl)amino]-6-(trans-4-methanesulphonylamino-cyclohexan-1-yloxy)-7-methoxy-quinazoline, 4-[(3-chloro-4-fluorophenyl)amino]-6-(tetrahydropyran-3-yloxy)-7-methoxy-quinazoline, 4-[(3-chloro-4-fluorophenyl)amino]-6-(1-methyl-piperidin-4-yloxy)-7-methoxy-quinazoline, 4-[(3-chloro-4-fluorophenyl)amino]-6-{1-[(morpholin-4-yl)carbonyl]-piperidin-4-yloxy}-7-methoxy-quinazoline, 4-[(3-chloro-4-fluorophenyl)amino]-6-{1-[(methoxymethyl)carbonyl]-piperidin-4-yl-oxy}-7-methoxy-quinazoline, 4-[(3-chloro-4-fluorophenyl)amino]-6-(piperidin-3-yloxy)-7-methoxy-quinazoline, 4-[(3-chloro-4-fluorophenyl)amino]-6-[1-(2-acetylamino-ethyl)-piperidin-4-yloxy]-7-methoxy-quinazoline, 4-[(3-chloro-4-fluorophenyl)amino]-6-(tetrahydropyran-4-yloxy)-7-ethoxy-quinazoline, 4-[(3-chloro-4-fluorophenyl)amino]-6-((S)-tetrahydrofuran-3-yloxy)-7-hydroxy-quinazoline, 4-[(3-chloro-4-fluorophenyl)amino]-6-(tetrahydropyran-4-yloxy)-7-(2-methoxy-ethoxy)-quinazoline, 4-[(3-chloro-4-fluorophenyl)amino]-6-{trans-4-[(dimethylamino)sulphonylamino]-cyclohexan-1-yloxy}-7-methoxy-quinazoline, 4-[(3-chloro-4-fluorophenyl)amino]-6-{trans-4-[(morpholin-4-yl)carbonylamino]-cyclohexan-1-yloxy}-7-methoxy-quinazoline, 4-[(3-chloro-4-fluorophenyl)amino]-6-{trans-4-[(morpholin-4-yl)sulphonylamino]-cyclohexan-1-yloxy}-7-methoxy-quinazoline, 4-[(3-chloro-4-fluorophenyl)amino]-6-(tetrahydropyran-4-yloxy)-7-(2-acetylamino-ethoxy)-quinazoline, 4-[(3-chloro-4-fluorophenyl)amino]-6-(tetrahydropyran-4-yloxy)-7-(2-methanesulphonylamino-ethoxy)-quinazoline, 4-[(3-chloro-4-fluorophenyl)amino]-6-{1-[(piperidin-1-yl)carbonyl]-piperidin-4-yloxy}-7-methoxy-quinazoline, 4-[(3-chloro-4-fluorophenyl)amino]-6-(1-aminocarbonylmethyl-piperidin-4-yloxy)-7-methoxy-quinazoline, 4-[(3-chloro-4-fluorophenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluorophenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluorophenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluorophenyl)amino]-6-(trans-4-ethanesulphonylamino-cyclohexan-1-yloxy)-7-methoxy-quinazoline, 4-[(3-chloro-4-fluorophenyl)amino]-6-(1-methanesulphonyl-piperidin-4-yloxy)-7-ethoxy-quinazoline, 4-[(3-chloro-4-fluorophenyl)amino]-6-(1-methanesulphonyl-piperidin-4-yloxy)-7-(2-methoxy-ethoxy)-quinazoline, 4-[(3-chloro-4-fluorophenyl)amino]-6-[1-(2-methoxy-acetyl)-piperidin-4-yloxy]-7-(2-methoxy-ethoxy)-quinazoline, 4-[(3-chloro-4-fluorophenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluorophenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluorophenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluorophenyl)amino]-6-{cis-4-[(morpholin-4-yl)carbonylamino]-cyclohexan-1-yloxy}-7-methoxy-quinazoline, 4-[(3-chloro-4-fluorophenyl)amino]-6-{1-[2-(2-oxopyrrolidin-1-yl)ethyl]-piperidin-4-yloxy}-7-methoxy-quinazoline, 4-[(3-chloro-4-fluorophenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluorophenyl)amino]-6-(1-methyl-piperidin-4-yloxy)-7(2-methoxy-ethoxy)-quinazoline, 4-[(3-chloro-4-fluorophenyl)amino]-6-(1-isopropyloxycarbonyl-piperidin-4-yloxy)-7-methoxy-quinazoline, 4-[(3-chloro-4-fluorophenyl)amino]-6-(cis-4-methylamino-cyclohexan-1-yloxy)-7-methoxy-quinazoline, 4-[(3-chloro-4-fluorophenyl)amino]-6-{cis-4-[N-(2-methoxy-acetyl)-N-methyl-amino-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluorophenyl)amino]-6-{1-[(cis-2,6-dimethyl-morpholin-4-yl)carbonyl]-piperidin-4-yloxy}-7-methoxy-quinazoline, 4-[(3-chloro-4-fluorophenyl)amino]-6-{1-[(2-methyl-morpholin-4-yl)carbonyl]-piperidin-4-yloxy}-7-methoxy-quinazoline, 4-[(3-chloro-4-fluorophenyl)amino]-6-{1-[(S,S)-(2-oxa-5-aza-bicyclo[2.2.1]hept-5-yl)carbonyl]-piperidin-4-yloxy}-7-methoxy-quinazoline, 4-[(3-chloro-4-fluorophenyl)amino]-6-{1-[(N-methyl-N-2-methoxyethyl-amino)carbonyl]-piperidin-4-yloxy}-7-methoxy-quinazoline, 4-[(3-chloro-4-fluorophenyl)amino]-6-(1-ethyl-piperidin-4-yloxy)-7-methoxy-quinazoline, 4-[(3-chloro-4-fluorophenyl)amino]-6-{1-[(2-methoxyethyl)carbonyl]-piperidin-4-yloxy}-7-methoxy-quinazoline, 4-[(3-chloro-4-fluorophenyl)amino]-6-{1-[(3-methoxypropyl-amino)-carbonyl]-piperidin-4-yloxy}-7-methoxy-quinazoline, 4-[(3-chloro-4-fluorophenyl)amino]-6-[cis-4-(N-methanesulphonyl-N-methyl-amino)cyclohexan-1-yloxy]-7-methoxy-quinazoline, 4-[(3-chloro-4-fluorophenyl)amino]-6-

[cis-4-(N-acetyl-N-methyl-amino)-cyclohexan-1-yloxy]-7-methoxy-quinazoline, 4-[(3-chloro-4-fluorophenyl)amino]-6-(trans-4-methylamino-cyclohexan-1-yloxy)-7-methoxy-quinazoline, 4-[(3-chloro-4-fluorophenyl)amino]-6-[trans-4-(N-methanesulphonyl-N-methyl-amino)-cyclohexan-1-yloxy]-7-methoxy-quinazoline, 4-[(3-chloro-4-fluorophenyl)amino]-6-(trans-4-dimethylamino-cyclohexan-1-yloxy)-7-methoxy-quinazoline, 4-[(3-chloro-4-fluorophenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluorophenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluorophenyl)amino]-6-(1-methanesulphonyl-piperidin-4-yloxy)-7-methoxy-chinazolin and 4-[(3-chloro-4-fluorophenyl)amino]-6-(1-cyano-piperidin-4-yloxy)-7-methoxy-quinazoline, optionally in the form of their racemates, enantiomers, diastereomers and optionally in the form of their pharmacologically acceptable acid addition salts, solvates or hydrates. The preferred acid addition salts according to the invention are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used here are preferably compounds selected from among bromocriptin, cabergolin, alpha-dihydroergocryptin, lisuride, pergolide, pramipexol, roxindol, ropinirol, talipexol, tergurid and viozan, optionally in the form of their racemates, enantiomers, diastereomers and optionally in the form of their pharmacologically acceptable acid addition salts, solvates or hydrates. The preferred acid addition salts according to the invention are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The H1-antihistamines used here are preferably compounds selected from among epinastine, cetirizine, azelastine, fexofenadine, levocabastine, loratadine, mizolastine, ketotifen, emedastine, dimetinden, clemastine, bamipine, cexchlorpheniramine, pheniramine, doxylamine, chlorphenoxamine, dimenhydrinate, diphenhydramine, promethazine, ebastine, desloratidine and meclozine, optionally in the form of their racemates, enantiomers, diastereomers and optionally in the form of their pharmacologically acceptable acid addition salts, solvates or hydrates. The preferred acid addition salts according to the invention are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Translation of Text in FIG. 13:

mittlere prozentuale Abweichung der Lichtintensitat vom Mittelwert über alle Dosierer=mean percentage deviation of the light intensity from the mean value over all the metering devices
prozentuale Abweichung=percentage deviation
Dosierernummer=number of metering devices

The invention claimed is:

1. A process for monitoring filling of a capsule or capsule part with a medicament, comprising the steps of:
   (a) holding and transporting the capsule or capsule part in a carrier or matrix;
   (b) filling the capsule or capsule part with a fill mass;
   (c) recording the contour of the fill mass by using an optical system to produce an image;
   (d) evaluating the fill mass by image analysis;
   (e) calculating optical characteristics of the capsule carrier or capsule matrix, including a capsule carrier location or matrix location, from digitized image data; and
   (f) adjusting the optical imaging system in a subsequent filling step such that a light intensity of the capsule carrier or capsule matrix assumes a desired value.

2. The process according to claim 1, wherein the optical characteristic of the capsule carrier or capsule matrix is a detected reflectivity.

3. The process according to claim 1, wherein the optical characteristic of the capsule carrier or capsule matrix is a detected transmittance.

4. The process according to claim 1, wherein the optical characteristic of the capsule carrier or capsule matrix is a detected mean image brightness.

5. The process according to claim 1, wherein an intensity of a light source is regulated such that the light intensity assumes the desired value.

6. The process according to claim 5, wherein the light source is a light emitting diode (LED) and a voltage of the LED is regulated by means of an algorithm.

7. The process according to claim 1, wherein a shutter speed of a camera which records the image of the capsule carrier or capsule matrix is between 10 microseconds and 100 microseconds so that the light intensity of the image recorded assumes the desired value.

8. The process according to claim 1, wherein an electrical channel amplification of a camera is regulated so that the light intensity assumes a desired value.

9. The process according to claim 1, wherein, in step (d), the image analysis of the contour fill mass is performed in order to evaluate the filling by a comparison with a given contour.

10. The process according to claim 1, wherein, in step (d), a recorded contour line is determined by curve fitting and comparison with the length of a contour line stored in a computer memory.

11. The process according to claim 1, wherein the image analysis involves a contrast which is increased and/or a grey scale or color gradation of an image which is reduced.

12. The process according to claim 1, wherein the image analysis involves the image being converted into a binary image starting from a threshold value.

13. The process according to claim 1, wherein the medicament is in powder form.

14. The process according to claim 1, wherein the filling is carried out using a pipette technique.

15. The process according to claim 1, wherein the image recorded is archived.

16. Apparatus for monitoring filling or continuous machine filling of a capsule or capsule part with a medicament, which comprises
   (a) a capsule filling machine operating to hold and transport the capsule or capsule part in a carrier or matrix, and to fill the capsule or capsule part with a fill mass;
   (b) an optical system for recording a contour of the fill mass of filled capsules to produce an image;
   (c) an image analysis system operating to evaluate the fill mass by image analysis; and
   (d) a control processor operating to: (i) calculate optical characteristics of the capsule carrier or capsule matrix, including a capsule carrier location or matrix location, from the image data, and (ii) adjust the optical imaging system in a subsequent filling step such that a light intensity of the capsule carrier or capsule matrix assumes a desired value.

17. The apparatus according to claim 16, further comprising a CCD (4) camera or a CMOS image converter with a refresh rate of between 10 Hertz and 1000 Hertz and a shutter speed of between 10 microseconds and 100 milliseconds.

18. The apparatus according to claim 16, wherein the apparatus has a control device that can be actuated by the control processor to adjust a diode voltage.

19. A method for controlling the process according to claim 1 by computer that has been programmed with software, comprising the steps of:
   reading out an image memory of a CCD camera or a C-MOS image converter
   calculating optical characteristics of a capsule carrier, including a mean integral light intensity of the images of an individual matrix
   converting grey scale or chrominance image matrices into binary image matrices
   applying an evaluating algorithm to the contour of the fill mass and quantifying the contour to produce a measured value
   storing the measured value and
   activating an ejector mechanism for defectively filled capsules.

20. The process according to claim 19, wherein a distribution of image matrix values is standardized to a spread of between 0 and 255.

21. The process according to claim 19, wherein an online visualization of the filled capsules is carried out.

22. The process according to claim 19, wherein a voltage of the light source is adjusted with the optical characteristics using a regulating algorithm.

23. The process according to claim 19, wherein characteristics of the optical control are compared with characteristics of a tare weight measurement.

24. The process according to claim 6, wherein the LED is a high performance LED.

25. The process according to claim 7, wherein the shutter speed is between 30 and 70 microseconds.

26. The process according to claim 7, wherein the shutter speed is an electrical shutter speed.

* * * * *